United States Patent [19]

Ohmori et al.

[11] 4,247,725

[45] Jan. 27, 1981

[54] METHOD OF REMOVING ACETYLENES FROM C$_4$-HYDROCARBON MIXTURE CONTAINING BUTADIENE

[75] Inventors: Tadashi Ohmori; Katuhiko Ishikawa, both of Yokohama, Japan

[73] Assignee: Nippon Oil Company, Ltd., Tokyo, Japan

[21] Appl. No.: 31,253

[22] Filed: Apr. 18, 1979

[30] Foreign Application Priority Data

Apr. 21, 1978 [JP] Japan .................................. 53-46681

[51] Int. Cl.$^3$ ............................................. C07C 7/167
[52] U.S. Cl. .................................................. 585/259
[58] Field of Search ........................ 585/259, 260, 261

[56] References Cited

U.S. PATENT DOCUMENTS 3,859,377  1/1975  Gross et al. ......................... 585/261

*Primary Examiner*—Curtis R. Davis
*Attorney, Agent, or Firm*—Jordan and Hamburg

[57] ABSTRACT

There is provided a method of selectively hydrogenating acetylenes in a C$_4$-hydrocarbon mixture containing butadiene for removing said acetylenes wherein a hydrogen containing gas and the liquid C$_4$-hydrocarbon mixture are continuously fed through the upper portion of a reactor filled with catalyst particles carrying one or more precious metals selected from the Group VIII elements of the Periodic Table, the hydrogen containing gas is present in the reactor forming a substantially continuous phase at the hydrogen partial pressure of less than 1.5 kg/cm$^2$.a, while the C$_4$-hydrocarbon mixture is allowed to flow down over the surfaces of the catalyst particles in the liquid form and to react at 5 to 80° C., and the reaction mixture is withdrawn through the bottom of the reactor.

10 Claims, No Drawings

METHOD OF REMOVING ACETYLENES FROM C$_4$-HYDROCARBON MIXTURE CONTAINING BUTADIENE

BACKGROUND OF THE INVENTION

1. Field of the Invention

The present invention relates to a method of selectively hydrogenating and removing acetylenes in a C$_4$-hydrocarbon mixture containing a substantial amount of butadiene with the minimal loss of butadiene.

2. Prior Art

A large amount of butadiene has been produced by the dehydrogenation of butane and/or butene, or may be derived by cracking various gaseous materials such as waste gases recovered from petroleum refining processes or a variety of hydrocarbons. Irrespective of the recovered butadiene sources, the purity of the thus recovered butadienes does not reach the level as required for using as starting materials for other organic compounds. They contain vinylacetylene, ethylacetylene and methylacetylene (Hereinafter referred to as acetylenes.) which can vary hardly be separated or removed by the ordinary fractional distillation. For this reason, it has been conventionally practised to hydrogenate a C$_4$-stream containing butadiene and acetylenes prior to or after the removal of butane and butene which may be easily separated. Such conventional catalytic hydrogenation has been carried out on a variety of hydrogenation catalysts in a vapor or liquid phase. However, in the conventional vapor phase or liquid phase processes, the aimed hydrogenation is often accompanied with undesirable hydrogenation of butadiene and/or polymerization thereof to result in considerable loss of the butadiene product. Moreover, in the vapor phase process which are carried out at a relatively high temperature of higher than 150° C., the activity of the catalyst is adversely lowered due to the side reaction, i.e. polymerization of butadiene. While if by the conventional liquid phase process acetylenes are hydrogenated to a very small amount level, a large quantity of butadiene will be lost due to the hydrogenation into monoolefins. On the other hand, if it is intended to suppress the loss of butadiene, the acetylene would be left unhydrogenated.

In fact, the amounts of acetylenes contained in the hydrocarbon mixture after hydrogenation may be controlled below the low level if the content of the acetylenes in the original starting hydrocarbon mixture is low, for example less than about 1,600 ppm. However, in such cases, the loss of butadiene would be increased inevitably if it is intended to improve the convertion ratio of acetylenes.

In the method disclosed in Japanese Patent Publication No. 2257/'63, a hydrocarbon mixture having a small acetylene contnet is used as starting material but the hydrogenation ratio of acetylenes is low as about 97% at best. Further, this prior art method is disadvantageous in that the hydrogenation reaction is carried out under the condition at which the partial pressure of hydrogen in the reaction system is high. If a hydrocarbon mixture of high acetylene content is used as starting material under such condition, the contained acetylenes can not be sufficiently removed as will be specifically shown hereinafter in the comparative examples.

Likewise in the method disclosed in Unexamined Japanese Patent Publication No. 95903/'74, the acetylene content after the hydrogenation reaction is higher than the order of hundreds ppm. We have examined and found that the acetylenes will not be removed sufficiently since the liquid reaction mixture is fed from the bottom of the reaction vessel upwardly and thus the catalytic reaction is carried out under the condition at which the reaction vessel is substantially full with liquid hydrocarbons although a gas mixture containing an inert gas and hydrogen is used in this prior art method.

Also in the method described in Japanese Patent Publication No. 19522/'75, the acetylene content after the hydrogenation reaction is higher than the order of hundreds ppm. In this prior art method, hydrogenation is effected while the liquid phase hydrocarbon being avoided to be saturated with hydrogen. However, this publication specifically describes that the liquid hydrocarbon is introduced from the lower portion of the reactor, and thus it is considered that the removal of the acetylenes would be insufficient likewise in the prior art methods described above. Although the Publication refers to the downward introduction of the liquified hydrocarbons briefly, but it fails to specifically describe in what manners of contact such downward introduction is used.

OBJECTS AND SUMMARY OF THE INVENTION

An object of the present invention is to provide a method of selectively hydrogenating and removing acetylenes in a C$_4$-hydrocarbon mixture containing butadiene below a possible minimal level while suppressing the loss of butadiene.

Another object of the present invention is to provide a method of selectively hydrogenating and removing acetylenes in a C$_4$-hydrocarbon mixture containing butadiene wherein 99% or more of said acetylenes is hydrogenated while suppressing the loss of butadiene.

A further object of the invention is to provide a method of selectively hydrogenating and removing acetylenes in a C$_4$-hydrocarbon mixture containing butadiene to reduce the acetylene content to a very low concentration of lower than 50 ppm while suppressing the loss of butadiene.

The above and other objects of the present invention will become apparent from the following description.

According to the present invention, there is provided an improved method of selectively hydrogenating and removing acetylenes from a C$_4$-hydrocarbon mixture containing butadiene, wherein a hydrogen containing gas and the liquid C$_4$-hydrocarbon mixture are continuously fed through the upper portion of a reactor filled with catalyst particles carrying one or more precious metals selected from the Group VIII elements of the Periodic Table, the hydrogen containing gas is present in the reactor forming a substantially continuous phase at the hydrogen partial pressure of less than 1.5 kg/cm.$^2$a, while the C$_4$-hydrocarbon mixture is allowed to flow down over the surfaces of the catalyst particles in the liquid form and to react at 5° to 80° C., and the reaction mixture is withdrawn through the bottom of the reactor.

DESCRIPTION OF THE INVENTION

The present invention will now be described in detail. The catalysts used in the method of the invention includes at least one precious metal of the Group VIII of the Periodic Table such as palladium, platinum, rhodium, ruthenium, iridium and osmium, preferably palladium or ruthenium or the compounds thereof supported on the surfaces of solid particle carriers (hereinafter referred to as the catalyst carrying a Group VIII metal). Typical examples of the solid particle carriers are inorganic porous carriers such as alumina, silica and silica-alumina. As the porous carrier, those having a relatively mean specific surface area, for instance the specific surface area of from 50 to 150 m$^2$/g, may be used. The precious metal or the compound thereof is supported on the surface of one of such carriers. One example of the preferable catalysts comprises palladium supported on an alumina, the content of palladium as the metallic component being 0.04 to 0.6% by weight. In addition to palladium, one or more metals such as copper, silver, chromium, lead, bismuth and gallium or oxides thereof may be contained in the catalyst as the promotor. Among these catalysts, some have particularly improved selectivities and thus suited for use in the method of the invention. These catalysts which extert particular selectivities in the hydrogenation treatment comprise supported catalysts in which at least one Group VIII precious metal is impregnated in the carrier. Specifically, these catalysts comprise a Group VIII precious metal or metals present in the thin surface shell of the carrier.

The method of the invention may be applied for a variety of C$_4$-hydrocarbon streams containing different amounts of butadiene and acetylenes, the latter being reduced by hydrogenation. The method of the invention is particularly effective for treating the C$_4$-hydrocarbon mixture of high acetylene content to reduce the acetylene content thereof to a trace, e.g. less than 50 ppm.

Typical mixed C$_4$-hydrocarbon stream composition suited for being treated by the method of the invention will be set forth below.

| Composition: | wt.% | | wt.% |
|---|---|---|---|
| Isobutane | 3 | 1,3-Butadiene | 30–50 |
| n-Butane | 5–6 | 1,2-Butadiene | 0.5–2 |
| Butenes | 40–60 | Vinylacetylene | 0.2–2.0 |
| | | Ethylacetylene | 0.05–1.0 |
| | | Methylacetylene | 0.05–0.8 |
| | | (Total of Acetylenes) | 0.3–3.8 |

In particular, the present invention is effective for treating C$_4$-hydrocarbon mixtures containing high concentration acetylenes, such as those containing acetylenes at the concentrations of about 5,000 to 20,000 ppm. In the method of the invention, a catalyst is charged in a tightly closed reactor provided with at least a starting material inlet port at the upper portion and with a reaction mixture outlet port at the lower portion thereof while allowing the catalyst to form a fixed bed.

The temperature in the reactor is maintained at 5° to 80° C. The reaction pressure is not particularly restricted, but it is preferred that the pressure be maintained within the range at which the starting C$_4$-hydrocarbon mixture is present in the liquid form, for example from 2 to 25 kg/cm.$^2$g.

The starting liquid C$_4$-hydrocarbon mixture and the hydrogen containing gas are fed from the upper portion of the reactor at the equal or lower temperature as that internally of the reactor.

The C$_4$-hydrocarbon mixtures used as the starting material in the method of the invention include a C$_4$-hydrocarbon mixture containing butadiene obtained by the process of thermal or steam cracking of petroleum or the like for producing olefins, and a hydrocarbon mixture containing butadiene which is obtained by dehydrogenation of butene and/or butane. As a special C$_4$-hydrocarbon mixture which may satisfactorily treated by the method of the invention, there may be mentioned a C$_4$-hydrocarbon mixture which is obtained as the by-product upon the extractive distillation of butadiene from the aforementioned C$_4$-hydrocarbon mixtures using a solvent and which contains about 20 to 80% by weight of butadiene and so large amounts of acetylenes such that the acetylene content reaches up to about 5 to 50% by weight.

Gaseous hydrogen may be used singly or together with an inert gaseous materials such as nitrogen, neon, helium, argon, methane and ethane, the content of said inert gaseous materials being for example less than 80 vol%, preferably 1 to 50 vol% and more preferably 3 to 30 vol%. Preferred inert gaseous additives are nitrogen and methane.

It is desired that the hydrogen gas should be refined by any of the known method so as not to contain a large amount of a compound which acts as catalyst poison against the Group VIII precious metal catalyst, such as hydrogen sulfide, sulfur dioxide, tiophene, mercaptan and carbon monoxide. Satisfactorily usable hydrogen streams may be readily obtainable from the petroleum refining and petrochemical plants.

According to the present invention, the thus fed hydrogen containing gas occupies a relatively large portion of the vacant space in the reaction vessel, for example 20 to 80 vol% thereof, and the hydrogen containing gas is normally present while forming a continuous phase in the reaction vessel.

The hydrocarbon mixture fed from the upper portion of the reaction vessel is allowed to flow over the surfaces of the catalyst particles filled in the reaction vessel so as to permit the reaction to proceed. In detail, the hydrogen containing gas present on the surfaces of the catalyst particles which are covered with thin films of liquid hydrocarbon permeates through said thin films of hydrocarbon to contact with the surfaces of the catalyst particles, whereupon the catalytic reaction takes place. The reaction is carried out at a temperature of from 5° to 80° C., as has been mentioned hereinbefore. If the temperature raises to higher than 80° C., the loss of butadiene due to polymerization increases and the catalyst becomes inactive shortly, hence the temperature raise of higher than the defined value should be avoided. (In the meanwhile, the method of the invention is not so sensitively affected by the temperature change of lower than about 65° C.) The most preferable temperature range for practising the method of the invention is from 15° to 65° C. The reaction pressure shall be essentially kept within the range at which the C$_4$-hydrocarbon mixture is kept to form the liquid phase, but the pressure does not affect the method of the invention critically provided that the hydrocarbon mixture forms the liquid phase. In general, the hydrogenation reaction may proceed at a pressure of from about 2 to 25 kg/cm.$^2$g. Preferable pressure is about 2 to 20 kg/cm.$^2$g. The weight base space velosity per hour of the liquid C$_4$-hydrocarbon mixture should be less than 20, preferably 5 to 15. The quantity of hydrogen fed to the reactor will be varied depending on the activity, life and selectivity of the specific kind of the used catalyst as well as the desired hydrogenation degree of the acetylenes. The method of the invention may be effected at the hydrogen content relative to the total quantity of the C₄-hydrocarbon stream ranging from 0.5 to 10 mol%, i.e. at the hydrogen molar ratio of 0.005 to 0.10, and the partial pressure of hydrogen in the reaction system shall be maintained at less than 1.5 kg/cm.$^2$a (absolute pressure), preferably from 0.05 to 1.0 kg/cm.$^2$a, and most preferably from 0.3 to 0.7 kg/cm.$^2$a. If the partial pressure of hydrogen becomes exceedingly high, butadiene is progressively hydrogenated to form butene, resulting in loss of butadiene.

The reaction mixture is withdrawn from the bottom of the reactor. The discharged reaction mixture is normally introduced into a vapor-liquid separator and the unreacted gas is separated from the liquid hydrocarbon mixture which has been treated to lower its acetylene content. The thus separated unreacted gas may be circulated for reuse directly or through a refining step. The separated liquid hydrocarbon mixture may be delivered to a subsequent butadiene recovery step, for example a butadiene refining and separating step by means of the extraction or extractive distillation process for profitable use.

The activity of the catalyst will be gradually lowered during the continuous operation of the method of the invention for a long time period, but it may be regenerated by burning in an air diluted with nitrogen or steam. In accordance with the method of the invention, it is possible to treat a C₄-hydrocarbon mixture containing acetylene at the order of more than 3,000 ppm to obtain a hydrocarbon mixture which contains only an extremely small amount of acetylenes, for example less than 50 ppm.

EXAMPLE OF THE INVENTION

The present invention will be more fully described with reference to the following examples. In the examples, respective operations were conducted in a liquid phase hydrogenation apparatus made of stainless steel comprising a reactor tube having an inner diameter of 2.5 cm and the length of 150 cm and provided with an external covering jacket in which warm water was circulated to control the temperature of the catalyst layer at a pre-determined temperature. The upper and lower portions of the reactor tube were filled with a carborundum filler for the sufficient preheating of the charged liquid. The catalyst was filled in the reactor tube to form a fixed bed. The starting C₄-hydrocarbon mixture was fed through a metering pump to the upper portion of the reactor tube in the liquid form and allowed to flow down over the surface of the catalyst. The controlled amounts of hydrogen and an inert gas stream were introduced through the upper portion of the reactor tube after being preheated. The pressure in the reaction system was maintained at a constant pressure level by means of an automatic air pressure regulator, and the reaction mixture flowing out of the reactor tube is cooled and then fed to a vapor-liquid separator, where it was separated into an unreacted gas (including the inert gas) and the reaction mixture. Tests on the activity of the catalyst were conducted for a few to 10 days.

EXAMPLE 1

The catalyst used in this Example was obtained by impregnating alumina having the specific surface area of 100 m²/g with 0.25 wt% of palladium. The composition of the C₄-hydrocarbon fraction used for the reaction is set forth below.

| | wt.% | | wt.% |
|---|---|---|---|
| Isobutane | 2.7 | 1,3-Butadiene | 40.8 |
| n-Butane | 6.3 | 1,2-Butadiene | 0.15 |
| isobutene | 26.5 | | |
| trans-butene-2 | 5.9 | Vinylacetylene | 0.58 |
| cis-butene-2 | 4.3 | Ethylacetylene | 0.25 |
| butene-1 | 12.5 | Methylacetylene | 0.17 |

Experiments were conducted respectively at 30° C. and 50° C., while the reaction pressure, WHSV and the hydrogen concentration were varied and the C₄-hydrocarbon fraction set forth above was intorduced to effect selective hydrogenation of the acetylenes. In this connection, the hydrogen concentration was changed by diluting hydrogen with an inert gas (nitrogen gas), and WHSV means the space velosity per hour per unit weight of the catalyst. The test results of the experiments conducted at 30° C. and 50° C. are shown in Tables 1 and 2, respectively.

TABLE 1

| | Experiments at 30° C. | | | | | | |
|---|---|---|---|---|---|---|---|
| | Comparative Example | | | Example of the Invention | | | |
| Run Number | 1 | 2 | 3 | 4 | 5 | 6 | 7 |
| Pressure (kg/cm.$^2$g) | 10 | 20 | 10 | 10 | 10 | 10 | 7 |
| WHSV | 8 | 10 | 7 | 9 | 9 | 9 | 8.5 |
| H₂/HC Molar Ratio | 5 | 5 | 4.9 | 4.0 | 5.3 | 5.2 | 5.2 |
| H₂ Concentration (mol%) | 100 | 100 | 30 | 10 | 5 | 10 | 3 |
| Residual Vinylacetylene (ppm) | 2400 | 2600 | 347 | 5 | 5 | ⎰ | ⎱ |
| Residual Ethylacetylene (ppm) | 1800 | 1820 | 377 | 12 | 6 | 42 | 41 |
| Residual Methylacetylene (ppm) | 1120 | 1210 | 532 | 31 | 20 | ⎱ | ⎰ |
| Loss of 1,3-Butadiene | 10.3 | 10.4 | 7.2 | 5.1 | 4.6 | 5.5 | 3.6 |
| Partial Pressure of H₂ (kg/cm.$^2$a) | 7.8 | 17.8 | 2.3 | 0.56 | 0.29 | 0.56 | 0.15 |

TABLE 2

| | Experiments at 50° C. | | | |
|---|---|---|---|---|
| | Comparative Example | | Example of the Invention | |
| Run Number | 8 | 9 | 10 | 11 |
| Pressure (kg/cm.$^2$g) | 10 | 20 | 10 | 20 |
| WHSV | 15 | 15.1 | 15.1 | 14.8 |
| H₂/HC Molar Ratio | 5.1 | 5 | 3.8 | 3.8 |
| H₂ Concentration (mol%) | 100 | 50 | 10 | 6.5 |
| Residual Vinylacetylene (ppm) | 2600 | 3100 | <5 | ⎰ |
| Residual Ethylacetylene (ppm) | 1910 | 2100 | 8 | 47 |
| Residual Methylacetylene | 1100 | 1410 | 36 | ⎱ |

TABLE 2-continued

| | Experiments at 50° C. | | | |
|---|---|---|---|---|
| | Comparative Example | | Example of the Invention | |
| Run Number | 8 | 9 | 10 | 11 |
| (ppm) Loss of 1,3-Butadinee | 11.7 | 11.8 | 4.8 | 5.8 |
| Partial Pressure of $H_2$ (kg/cm.$^2$a) | 5.4 | 7.7 | 0.54 | 1.00 |

As will be apparent from the test results of the Experiments set forth above according to the method of the present invention, it is possible to use a $C_4$-hydrocarbon fraction containing butadiene and high concentration of acetylenes as starting material to selectively hydrogenate the acetylenes while suppressing the loss of butadiene thereby to obtain a $C_4$-hydrocarbon fraction which contains less than 50 ppm acetylenes.

While the present invention has been described with reference to specific examples thereof, the invention may be embodied in other specific forms without departing from the spirit or essential characteristic thereof. The examples set forth above are therefore to be considered in all aspects as illustrative and not restrictive, the scope of the invention being indicated by the appended claims rather than by the foregoing description, and all changes which come within the meaning and range of equivalency of the claims are therefore intended to be embraced therein.

What is claimed is:

1. In a method of selectively hydrogenating acetylenes in a $C_4$-hydrocarbon mixture containing butadiene for removing said acetylenes, an improved method wherein a hydrogen containing gas and the liquid $C_4$-hydrocarbon mixture are continuously fed through the upper portion of a reactor filled with catalyst particles carrying one or more precious metals selected from the Group VIII elements of the Periodic Table, the hydrogen containing gas is present in the reactor forming a substantially continuous phase at the hydrogen partial pressure of less than 1.5 kg/cm.$^2$a, while the $C_4$-hydrocarbon mixture is allowed to flow down over the surfaces of the catalyst particles in the liquid form and to react at 5° to 80° C., and the reaction mixture is withdrawn through the bottom of the reactor.

2. The method as claimed in claim 1, wherein said $C_4$-hydrocarbon mixture is selected from the group consisting of a $C_4$-hydrocarbon mixture containing butadiene obtained by cracking petroleum for the production of olefins, a hydrocarbon mixture containing butadiene obtained by dehydrogenation of butene and/or butane, and a hydrocarbon mixture containing butadiene obtained as by-product upon extractive distillation of butadiene from a $C_4$-hydrocarbon mixture by the use of a solvent.

3. The method as claimed in claim 2, wherein said $C_4$-hydrocarbon mixture containing butadiene is a mixture composed of butanes, butenes, butadienes and acetylenes.

4. The method as claimed in claim 1, wherein said Group VIII precious metal is one or more selected from the group consisting of palladium, platinum, rhodium, ruthenium, iridium and osmium.

5. The method as claimed in claim 1, wherein said hydrogen containing gas is selected from the group consisting of gaseous hydrogen, and a mixture thereof with at least one of an inert gas selected from nitrogen, helium, neon, argon, methane and ethane.

6. The method as claimed in claim 1, 2, 3, 4 or 5, wherein said hydrogenation is effected at a pressure of from 2 to 25 kg/cm.$^2$g.

7. The method as claimed in claim 1, 2, 3, 4 or 5, wherein said liquid $C_4$-hydrocarbon mixture is fed at the weight base space velocity per hour of less than 20.

8. The method as claimed in claim 1, 2, 3, 4 or 5, wherein a $C_4$-hydrocarbon mixture containing 3,000 ppm or more acetylenes is used as the starting material and wherein a reaction mixture containing 50 ppm or less acetylenes is withdrawn from the bottom of the reactor.

9. The method as claimed in claim 1, wherein said precious metals are present in the thin surface shell of said catalyst particles.

10. The method as claimed in claim 1, wherein the surfaces of said catalyst particles are covered with thin films of said $C_4$-hydrocarbon mixture.

* * * * *